US007485454B1

(12) United States Patent
Jury et al.

(10) Patent No.: US 7,485,454 B1
(45) Date of Patent: Feb. 3, 2009

(54) MICROREACTOR

(75) Inventors: Andrey Zarur Jury, Emeryville, CA (US); Mark D. Angelino, Wilmington, DE (US)

(73) Assignee: BioProcessors Corp., Woburn, MA (US)

( * ) Notice: Subject to any disclaimer, the term of this patent is extended or adjusted under 35 U.S.C. 154(b) by 0 days.

(21) Appl. No.: 09/707,852

(22) Filed: Nov. 7, 2000

Related U.S. Application Data (60) Provisional application No. 60/188,275, filed on Mar. 10, 2000.

(51) Int. Cl.
*C12M 1/12* (2006.01)

(52) U.S. Cl. ............. 435/288.5; 435/286.7; 435/294.1; 435/297.1; 435/297.5

(58) Field of Classification Search .......... 422/129, 422/131, 101, 102; 435/286.7, 287.2, 288.5, 435/288.6, 289.1, 294.1, 297.1, 297.5; 204/403, 204/600, 601; *C12M 1/12*
See application file for complete search history.

(56) References Cited

U.S. PATENT DOCUMENTS

| | | | |
|---|---|---|---|
| 4,038,151 A | 7/1977 | Fadler et al. |
| 4,116,775 A | 9/1978 | Charles et al. |
| 4,118,280 A | 10/1978 | Charles et al. |
| 4,318,994 A | 3/1982 | Meyer et al. |
| 4,720,462 A | 1/1988 | Rosenson |
| 4,756,884 A | 7/1988 | Hillman et al. |
| 4,839,292 A | 6/1989 | Cremonese |
| 4,952,373 A | 8/1990 | Sugarman et al. |
| 5,004,685 A | 4/1991 | Arai et al. |
| 5,047,213 A | 9/1991 | Finlan et al. |
| 5,051,237 A | 9/1991 | Grenner et al. |
| 5,173,225 A | 12/1992 | Range et al. |
| 5,219,762 A | 6/1993 | Katamine et al. |
| 5,252,294 A | 10/1993 | Kroy et al. |
| 5,254,143 A | 10/1993 | Anazawa et al. |
| 5,278,048 A | 1/1994 | Parce et al. |
| 5,387,329 A | 2/1995 | Foos et al. |
| 5,424,209 A | 6/1995 | Kearney |
| 5,430,542 A | 7/1995 | Shepherd |

(Continued)

FOREIGN PATENT DOCUMENTS

DE        19728520 A1       1/1999

(Continued)

OTHER PUBLICATIONS

Office Action dated May 19, 2004 from U.S. Appl. No. 10/119,917.

(Continued)

*Primary Examiner*—David A Redding
(74) *Attorney, Agent, or Firm*—Wolf Greenfield & Sacks, P.C.

(57) ABSTRACT

Chemical and biological reactors, including microreactors, are provided. Exemplary reactors include a plurality of reactors operable in parallel, where each reactor has a small volume and, together, the reactors produce a large volume of product. Reaction systems can include mixing chambers, heating/dispersion units, reaction chambers, and separation units. Components of the reactors can be readily formed from a variety of materials. For example, they can be etched from silicon. Components are connectable to and separable from each other to form a variety of types of reactors, and the reactors can be attachable to and separable from each other to add significant flexibility in parallel and/or series reactor operation.

6 Claims, 7 Drawing Sheets

U.S. PATENT DOCUMENTS

| | | |
|---|---|---|
| 5,436,129 A | 7/1995 | Stapleton |
| 5,449,617 A | 9/1995 | Falkenberg et al. |
| 5,478,751 A | 12/1995 | Oosta et al. |
| 5,496,697 A | 3/1996 | Parce et al. |
| 5,534,328 A | 7/1996 | Ashmead et al. ............ 428/166 |
| 5,576,211 A | 11/1996 | Falkenberg et al. |
| 5,580,523 A | 12/1996 | Bard |
| 5,587,128 A | 12/1996 | Wilding et al. ................. 422/50 |
| 5,589,350 A | 12/1996 | Bochner |
| 5,593,632 A | 1/1997 | Kagawa |
| 5,595,712 A | 1/1997 | Harbster et al. |
| 5,602,028 A | 2/1997 | Minchinton |
| 5,612,188 A | 3/1997 | Shuler et al. |
| 5,632,957 A | 5/1997 | Heller et al. ................. 422/682 |
| 5,639,423 A | 6/1997 | Northrup |
| 5,646,039 A | 7/1997 | Northrup |
| 5,674,742 A | 10/1997 | Northrup et al. ......... 435/286.5 |
| 5,705,018 A | 1/1998 | Hartley ........................ 156/345 |
| 5,744,366 A | 4/1998 | Kricka et al. |
| 5,800,785 A | 9/1998 | Bochner |
| 5,800,788 A | 9/1998 | Douren |
| 5,840,258 A | 11/1998 | Hyppanen |
| 5,842,787 A | 12/1998 | Kopf-Sill et al. |
| 5,846,396 A | 12/1998 | Zanzucchi et al. .......... 204/601 |
| 5,856,174 A | 1/1999 | Lipshutz |
| 5,858,770 A | 1/1999 | Perlman |
| 5,916,812 A | 6/1999 | Chen et al. |
| 5,928,880 A | 7/1999 | Wilding et al. ............. 435/7.21 |
| 5,942,443 A | 8/1999 | Parce et al. ................. 436/524 |
| 5,957,579 A | 9/1999 | Kopf-Sill et al. |
| 5,958,694 A | 9/1999 | Nikiforov |
| 5,964,995 A | 10/1999 | Nikiforov et al. |
| 5,965,092 A | 10/1999 | Chatterjee et al. ........... 422/130 |
| 5,972,187 A | 10/1999 | Parce et al. |
| 5,976,472 A | 11/1999 | Chatterjee et al. |
| 5,981,211 A | 11/1999 | Hu et al. |
| 5,985,119 A | 11/1999 | Zanzucchi et al. .......... 204/450 |
| 5,989,835 A | 11/1999 | Dunlay et al. |
| 5,992,769 A | 11/1999 | Wise et al. ................... 239/548 |
| 5,993,750 A | 11/1999 | Ghosh et al. ................. 422/191 |
| 6,001,352 A | 12/1999 | Boyan et al. |
| 6,001,585 A | 12/1999 | Gramer |
| 6,008,010 A | 12/1999 | Greenberger et al. |
| 6,012,902 A | 1/2000 | Parce |
| 6,025,601 A | 2/2000 | Trulson et al. |
| 6,042,710 A | 3/2000 | Dubrow |
| 6,043,080 A | 3/2000 | Lipshutz et al. |
| 6,046,056 A | 4/2000 | Parce et al. |
| 6,090,251 A | 7/2000 | Sundberg et al. |
| 6,103,199 A | 8/2000 | Bjornson et al. |
| 6,103,479 A | 8/2000 | Taylor |
| 6,107,044 A | 8/2000 | Nikiforov |
| 6,117,643 A | 9/2000 | Simpson et al. |
| 6,126,946 A | 10/2000 | Counsell et al. |
| 6,143,247 A | 11/2000 | Sheppard, Jr. et al. |
| 6,148,968 A | 11/2000 | Davison |
| 6,150,180 A | 11/2000 | Parce et al. |
| 6,167,910 B1 | 1/2001 | Chow |
| 6,171,067 B1 | 1/2001 | Parce |
| 6,171,850 B1 | 1/2001 | Nagle et al. |
| 6,174,675 B1 | 1/2001 | Chow et al. |
| 6,176,962 B1 | 1/2001 | Soane et al. |
| 6,184,029 B1 | 2/2001 | Wilding et al. |
| 6,186,660 B1 | 2/2001 | Kopf-Sill et al. |
| 6,193,647 B1 | 2/2001 | Beebe et al. |
| 6,221,226 B1 | 4/2001 | Kopf-Sill |
| 6,221,654 B1 | 4/2001 | Quake et al. |
| 6,235,175 B1 | 5/2001 | Dubrow et al. |
| 6,238,538 B1 | 5/2001 | Parce et al. |
| 6,245,295 B1 | 6/2001 | Chen et al. |
| 6,251,343 B1 | 6/2001 | Dubrow et al. |
| 6,264,892 B1 | 7/2001 | Kaltenbach et al. |
| 6,267,858 B1 | 7/2001 | Parce et al. |
| 6,274,089 B1 | 8/2001 | Chow et al. |
| 6,274,337 B1 | 8/2001 | Parce et al. |
| 6,319,469 B1 | 11/2001 | Mian et al. |
| 6,319,474 B1 | 11/2001 | Krulevitch et al. |
| 6,321,791 B1 | 11/2001 | Chow |
| 6,338,790 B1 | 1/2002 | Feldman et al. |
| 6,339,023 B1 | 1/2002 | Kitazaki et al. |
| 6,346,413 B1 | 2/2002 | Fodor et al. |
| 6,368,871 B1 | 4/2002 | Christel et al. |
| 6,377,721 B1 | 4/2002 | Walt et al. |
| 6,387,651 B1 | 5/2002 | Bochner et al. |
| 6,410,309 B1 | 6/2002 | Barbera-Guillem et al. |
| 6,440,722 B1 | 8/2002 | Knapp et al. |
| 6,455,310 B1 | 9/2002 | Barbera-Guillem |
| 6,461,812 B2 | 10/2002 | Barth et al. |
| 6,461,861 B2 | 10/2002 | Schilling et al. |
| 6,479,252 B1 | 11/2002 | Barbera-Guillem et al. |
| 6,479,299 B1 | 11/2002 | Parce et al. |
| 6,488,895 B1 | 12/2002 | Kennedy |
| 6,488,897 B2 | 12/2002 | Dubrow et al. |
| 6,494,230 B2 | 12/2002 | Chow |
| 6,494,614 B1 | 12/2002 | Bennett et al. |
| 6,509,085 B1 | 1/2003 | Kennedy |
| 6,517,234 B1 | 2/2003 | Kopf-Sill et al. |
| 6,534,013 B1 | 3/2003 | Kennedy |
| 6,537,799 B2 | 3/2003 | Chow et al. |
| 6,542,863 B1 | 4/2003 | Surucu |
| 6,547,941 B2 | 4/2003 | Kopf-Sill et al. |
| 6,551,841 B1 * | 4/2003 | Wilding et al. ............... 436/518 |
| 6,552,784 B1 | 4/2003 | Dietz et al. |
| 6,555,067 B1 | 4/2003 | Gandhi et al. |
| 6,555,365 B2 | 4/2003 | Barbera-Guillem et al. |
| 6,558,944 B1 | 5/2003 | Parce et al. |
| 6,569,674 B1 | 5/2003 | McGarry |
| 6,582,576 B1 | 6/2003 | Chow et al. |
| 6,592,733 B1 | 7/2003 | Foley et al. |
| 6,592,821 B1 | 7/2003 | Wada et al. |
| 6,597,438 B1 | 7/2003 | Cabuz et al. |
| 6,599,436 B1 | 7/2003 | Matzke et al. |
| 6,602,714 B1 | 8/2003 | Tagge et al. |
| 6,613,581 B1 | 9/2003 | Wada et al. |
| 6,614,030 B2 | 9/2003 | Maher et al. |
| 6,632,656 B1 | 10/2003 | Thomas et al. |
| 6,642,046 B1 | 11/2003 | McGarry et al. |
| 6,645,432 B1 | 11/2003 | Anderson et al. |
| 6,648,015 B1 | 11/2003 | Chow |
| 6,653,124 B1 | 11/2003 | Freeman |
| 6,699,665 B1 | 3/2004 | Kim et al. |
| 6,716,588 B2 | 4/2004 | Sammak et al. |
| 6,716,620 B2 | 4/2004 | Bashir et al. |
| 6,716,629 B2 | 4/2004 | Hess et al. |
| 6,734,436 B2 | 5/2004 | Faris et al. |
| 6,742,661 B1 | 6/2004 | Schulte et al. |
| 6,743,633 B1 | 6/2004 | Hunter |
| 6,756,019 B1 | 6/2004 | Dubrow et al. |
| 6,761,962 B2 | 7/2004 | Bentsen et al. |
| 6,770,434 B2 | 8/2004 | Shvets et al. |
| 6,790,652 B1 | 9/2004 | Terry et al. |
| 6,806,543 B2 | 10/2004 | Yamakawa et al. |
| 6,811,752 B2 | 11/2004 | Barbera-Guillem |
| 6,818,436 B2 | 11/2004 | Yamamoto et al. |
| 6,821,772 B2 | 11/2004 | Barbera-Guillem et al. |
| 6,827,095 B2 | 12/2004 | O'Connor et al. |
| 6,837,926 B2 | 1/2005 | David |
| 6,837,927 B2 | 1/2005 | David |
| 6,848,462 B2 | 2/2005 | Covington et al. |
| 6,849,463 B2 | 2/2005 | Santini, Jr. et al. |
| 6,857,449 B1 | 2/2005 | Chow |
| 6,884,580 B2 | 4/2005 | Caren et al. |
| 6,919,046 B2 | 7/2005 | O'Connor et al. |
| 6,937,330 B2 | 8/2005 | Dietz et al. |

| | | |
|---|---|---|
| 6,949,377 B2 | 9/2005 | Ho |
| 6,981,522 B2 | 1/2006 | O'Connor et al. |
| 6,994,749 B2 | 2/2006 | David |
| 7,005,292 B2 | 2/2006 | Wilding et al. |
| 7,026,124 B2 | 4/2006 | Barth et al. |
| 7,028,536 B2 | 4/2006 | Karp et al. |
| 7,033,474 B1 | 4/2006 | Dubrow et al. |
| 7,033,819 B2 | 4/2006 | Kim et al. |
| 7,033,821 B2 | 4/2006 | Kim et al. |
| 7,052,880 B2 | 5/2006 | McEntee |
| 2001/0024821 A1 | 9/2001 | Potter |
| 2002/0029814 A1 | 3/2002 | Unger et al. |
| 2002/0055166 A1 | 5/2002 | Cannon |
| 2002/0068358 A1 | 6/2002 | Campbell et al. |
| 2002/0069619 A1 | 6/2002 | Abasolo et al. |
| 2002/0069620 A1 | 6/2002 | Abasolo |
| 2002/0072113 A1 | 6/2002 | Barbera-Guillem et al. |
| 2002/0072116 A1 | 6/2002 | Bhatia et al. |
| 2002/0086439 A1 | 7/2002 | Nagle et al. |
| 2002/0092767 A1 | 7/2002 | Bjornson et al. |
| 2002/0097633 A1 | 7/2002 | O'Connor et al. |
| 2002/0100714 A1 | 8/2002 | Staats |
| 2002/0110905 A1 | 8/2002 | Barbera-Guillem et al. |
| 2002/0117517 A1 | 8/2002 | Unger et al. |
| 2002/0146817 A1 | 10/2002 | Cannon et al. |
| 2002/0168757 A1 | 11/2002 | Kirk et al. |
| 2002/0172621 A1 | 11/2002 | Barbera-Guillem |
| 2002/0176804 A1 | 11/2002 | Strand et al. |
| 2002/0177159 A1 | 11/2002 | Bedilion et al. |
| 2002/0182749 A1 | 12/2002 | Singh et al. |
| 2002/0185183 A1 | 12/2002 | O'Connor et al. |
| 2002/0185431 A1 | 12/2002 | Karp |
| 2002/0187074 A1 | 12/2002 | O'Connor et al. |
| 2002/0187560 A1 | 12/2002 | Pezzuto et al. |
| 2002/0197603 A1 | 12/2002 | Chow et al. |
| 2003/0005877 A1 | 1/2003 | David |
| 2003/0008308 A1 | 1/2003 | Enzelberger et al. |
| 2003/0008388 A1 | 1/2003 | Barbera-Guillem et al. |
| 2003/0013203 A1 | 1/2003 | Jedrzejewski et al. |
| 2003/0015429 A1 | 1/2003 | Dubrow et al. |
| 2003/0022153 A1 | 1/2003 | Kirk et al. |
| 2003/0022197 A1 | 1/2003 | Kirk et al. |
| 2003/0022203 A1 | 1/2003 | Kumar |
| 2003/0022269 A1 | 1/2003 | Kirk et al. |
| 2003/0022362 A1 | 1/2003 | Kirk et al. |
| 2003/0026740 A1 | 2/2003 | Staats |
| 2003/0040104 A1 | 2/2003 | Barbera-Guillem |
| 2003/0049862 A1 | 3/2003 | He et al. |
| 2003/0077817 A1 | 4/2003 | Zarur et al. |
| 2003/0082632 A1 | 5/2003 | Shumate |
| 2003/0082795 A1 | 5/2003 | Shuler et al. |
| 2003/0091476 A1 | 5/2003 | Zhou et al. |
| 2003/0104512 A1 | 6/2003 | Freeman et al. |
| 2003/0129646 A1 | 7/2003 | Briscoe et al. |
| 2003/0129665 A1 | 7/2003 | Selvan et al. |
| 2003/0134431 A1 | 7/2003 | Parce et al. |
| 2003/0138819 A1 | 7/2003 | Gong et al. |
| 2003/0138829 A1 | 7/2003 | Unger et al. |
| 2003/0142291 A1 | 7/2003 | Padmanabhan et al. |
| 2003/0175947 A1 | 9/2003 | Liu et al. |
| 2004/0002131 A1 | 1/2004 | Kim et al. |
| 2004/0029213 A1 | 2/2004 | Callahan et al. |
| 2004/0029266 A1 | 2/2004 | Barbera-Guillem |
| 2004/0053403 A1 | 3/2004 | Jedrzejewski et al. |
| 2004/0058407 A1 | 3/2004 | Miller et al. |
| 2004/0058408 A1 | 3/2004 | Thomas et al. |
| 2004/0058437 A1 | 3/2004 | Rodgers et al. |
| 2004/0067577 A1 | 4/2004 | Wilson et al. |
| 2004/0072278 A1 | 4/2004 | Chou et al. |
| 2004/0072363 A1 | 4/2004 | Schembri |
| 2004/0077075 A1 | 4/2004 | Jensen et al. |
| 2004/0121454 A1 | 6/2004 | Jury et al. |
| 2004/0132166 A1 | 7/2004 | Miller et al. |
| 2004/0197905 A1 | 10/2004 | Hafeman |
| 2004/0224380 A1 | 11/2004 | Chou et al. |
| 2004/0228771 A1 | 11/2004 | Zhou et al. |
| 2004/0229349 A1 | 11/2004 | Daridon |
| 2004/0229378 A1 | 11/2004 | Schulte et al. |
| 2004/0234940 A1 | 11/2004 | Van Der Steen et al. |
| 2004/0259237 A1 | 12/2004 | Kellogg et al. |
| 2005/0014129 A1 | 1/2005 | Cliffel et al. |
| 2005/0026134 A1 | 2/2005 | Miller et al. |
| 2005/0026273 A1 | 2/2005 | Zarur et al. |
| 2005/0032204 A1 | 2/2005 | Rodgers et al. |
| 2005/0037471 A1 | 2/2005 | Liu et al. |
| 2005/0047967 A1 | 3/2005 | Chuang et al. |
| 2005/0089993 A1 | 4/2005 | Boccazzi et al. |
| 2005/0106714 A1 | 5/2005 | Zarur et al. |
| 2005/0255003 A1 | 11/2005 | Summersgill et al. |
| 2005/0266582 A1 | 12/2005 | Modlin et al. |
| 2005/0271560 A1 | 12/2005 | Rodgers et al. |
| 2005/0277187 A1 | 12/2005 | Johnson et al. |
| 2005/0287673 A1 | 12/2005 | Johnson et al. |
| 2006/0019333 A1 | 1/2006 | Rodgers et al. |
| 2006/0199260 A1 | 9/2006 | Zhang et al. |
| 2006/0270023 A1 | 11/2006 | LeDuc et al. |

FOREIGN PATENT DOCUMENTS

| | | |
|---|---|---|
| EP | 1 221 617 A2 | 7/2002 |
| EP | 1 226 871 A2 | 7/2002 |
| JP | 62-079831 | 4/1987 |
| JP | 62079831 | 4/1987 |
| JP | 2000 005581 A | 1/2000 |
| JP | 2001 129557 A | 5/2001 |
| JP | 2001 157897 A | 6/2001 |
| WO | WO 94/11489 A1 | 5/1994 |
| WO | WO 99/17093 | 4/1999 |
| WO | WO 99/17093 A1 | 4/1999 |
| WO | WO 99/34909 A1 | 7/1999 |
| WO | WO 99/55827 A1 | 11/1999 |
| WO | WO 99/57310 A2 | 11/1999 |
| WO | WO 00/03805 A1 | 1/2000 |
| WO | WO 00/17624 A2 | 3/2000 |
| WO | WO 00/43552 A2 | 7/2000 |
| WO | WO 00/56870 A1 | 9/2000 |
| WO | WO 01/07891 A2 | 2/2001 |
| WO | WO 01/38559 | 5/2001 |
| WO | WO 01/38559 A2 | 5/2001 |
| WO | WO 01/92462 A1 | 6/2001 |
| WO | WO 01/54813 A2 | 8/2001 |
| WO | WO 01/68257 A1 | 9/2001 |
| WO | WO 01/92870 A2 | 12/2001 |
| WO | WO 02/11880 A2 | 2/2002 |
| WO | WO 02/14539 A1 | 2/2002 |
| WO | WO 02/057200 | 7/2002 |
| WO | WO 02/057200 A2 | 7/2002 |
| WO | WO 02/083852 A2 | 10/2002 |
| WO | WO 02/100542 A1 | 12/2002 |
| WO | WO 03/035824 A1 | 5/2003 |
| WO | WO 03/066876 A2 | 8/2003 |
| WO | WO 03/093406 A2 | 11/2003 |
| WO | WO 03/103813 A2 | 12/2003 |
| WO | WO 03/104384 A1 | 12/2003 |
| WO | WO 2004/009226 A1 | 1/2004 |
| WO | WO 2004/016727 A1 | 2/2004 |
| WO | WO 2004/016729 A2 | 2/2004 |
| WO | WO 2004/069983 A2 | 8/2004 |
| WO | WO 2004/076647 A2 | 9/2004 |
| WO | WO 2004/112946 A2 | 12/2004 |
| WO | WO 2005/120698 | 12/2005 |
| WO | WO 2005/121307 | 12/2005 |
| WO | WO 2005/121310 | 12/2005 |

OTHER PUBLICATIONS

Office Action dated Oct. 6, 2003 from U.S. Appl. No. 10/119,917.

Hediger, S., et al., "Biosystem for the culture and characterisation of epithelial cell tissues," *Sensors and Actuators* B 63 (2000) pp. 63-73.

International Search Report for International Application Serial No. PCT/US01/07679, published as International Publication No. WO 01/68257, dated Jun. 8, 2001.

Written Opinion for International Application Serial No. PCT/US01/07679, published as International Publication No. WO 01/68257, dated Jan. 11, 2002.

International Preliminary Examination Report for International Application Serial No. PCT/US01/07679, published as International Publication No. WO 01/68257, dated May 20, 2002.

International Search Report for International Application Serial No. PCT/US02/11422, published as International Publication No. WO 02/083852, dated Mar. 12, 2003.

Written Opinion for International Application Serial No. PCT/US02/11422, published as International Publication No. WO 02/083852, dated May 5, 2003.

International Preliminary Examination Report for International Application Serial No. PCT/US02/11422, published as International Publication No. WO 02/083852, dated Nov. 21, 2003.

Searby et al., "Space Life Support From The Cellular Perspective," ICES Proceedings, May 2001.

Office Action dated Jan. 11, 2005 from U.S. Appl. No. 10/119,917.

Hayakawa, Y., et. al, "Synthesis of Poly(phenylacetylene)s Containing Trifluoromethyl Group for Gas Permeable Membrane," *Journal of Polymer Science: Part A: Polymer Chemistry*, vol. 30, pp. 873-877 (1992).

Pinnau, I., et al., "Influence of Side-Chain Length on the Gas Permeation Properties of Poly(2-alkylacetylenes)," *Macromolecules*, vol. 37, pp. 2823-2828 (2004).

Office Action dated Feb. 7, 2006 from U.S. Appl. No. 10/119,917.

International Search Report dated Jan. 12, 2004 in International Application No. PCT/US03/17816.

Hayakawa, Y., et al. "Synthesis of Poly (phenylacetylene)s Containing Trifluoromethyl Groups for Gas Permeable Membrane," *Journal of Polymer Science*, vol. 30, pp. 873-877.

Pinnau, I., et al. "Influence of Side-Chain Length on the Gas Permeation Properties of Poly(2-alkylacetylenes)," *Macromolecules*, vol. 37, pp. 2823-2828.

International Search Report dated Dec. 2, 2005, for PCT/US05/019914, filed Jun. 7, 2005.

Office Action dated Apr. 17, 2007 in U.S. Appl. No. 10/664,046.

Office Action dated Jul. 24, 2007 in U.S. Appl. No. 10/664,067.

\* cited by examiner

MICROREACTOR

RELATED APPLICATION

This application claims the benefit of priority under 35 U.S.C. §119(e) of co-pending U.S. Provisional Patent Application Ser. No. 60/188,275, filed Mar. 10, 2000.

FIELD OF THE INVENTION

The present invention relates generally to chemical or biochemical microreactors, and more particularly to a microreactor for the production of the product of a chemical or biochemical reaction, including a plurality of individuated microreactors constructed to operate in parallel.

BACKGROUND OF THE INVENTION

A wide variety of reaction systems are known for the production of the product of chemical or biochemical reactions. Chemical plants involving catalysis, biochemical fermenters, pharmaceutical production plants, and a host of other systems are well-known.

Systems for housing chemical and biochemical reactions not necessarily for the production of product also are known. For example, continuous-flow systems for the detection of various analytes in bodily fluids including blood, such as oxygen, glucose, and the like are well known.

In many of these and other systems, the capacity of the system (the volume of material that the system is designed to produce, process, or analyze) is adjusted in accordance with the volume of reactant, product, or analyte desirably processed or analyzed. For example, in large-scale chemical or pharmaceutical production, reactors are generally made as large as possible to generate as large a volume of product as possible. Conversely, in many areas of clinical diagnosis, where it is desirable to obtain as much information as possible from as small a physiological sample as possible (e.g., from a tiny drop of blood), it is a goal to minimize the size of reaction chambers of sensors. Several examples of small-scale reactor systems, including those used in clinical diagnoses and other applications, follow.

U.S. Pat. No. 5,387,329 (Foos, et al.; Feb. 7, 1995) describes an extended use planar clinical sensor for sensing oxygen levels in a blood sample.

U.S. Pat. No. 5,985,119 (Zanzucchi, et al.; Nov. 16, 1999) describes small reaction cells for performing synthetic processes in a liquid distribution system. A variety of chemical reactions including catabolic, anabolic reactions, oxidation, reduction, DNA synthesis, etc. are described.

U.S. Pat. No. 5,674,742 (Northrup, et al.; Oct. 7, 1997) describes an integrated microfabricated instrument for manipulation, reaction, and detection of microliter to picoliter samples. The system purported by is suitable for biochemical reactions, particularly DNA-based reactions such as the polymerase chain reaction.

U.S. Pat. No. 5,993,750 (Ghosh, et al.; Nov. 30, 1999) describes an integrated micro-ceramic chemical plant having a unitary ceramic body formed from multiple ceramic layers in the green state which are sintered together defining a mixing chamber, passages for delivering and reacting fluids, and means for delivering mixed chemicals to exit from the device.

Biochemical processing typically involve the use of a live microorganism (cells) to produce a substance of interest. Biochemical and biomedical processing account for about 50% of the total drug, protein and raw amino-acid production worldwide. Approximately 90% of the research and development (R&D) budget in pharmaceutical industries is currently spent in biotechnology areas.

Currently bioreactors (fermentors) have several significant operational limitations. The most important being maximum reactor size which is linked to aeration properties, to nutrient distribution, and to heat transfer properties. During the progression of fermentation, the growth rate for cells accelerates, and the measures required to supply the necessary nutrients and oxygen sets physical and mechanical constraints on the vessel within which the cells are contained. Powerful and costly drives are needed to compensate for inefficient mixing and low mass-transfer rates. Additionally, as metabolism of cells accelerates, the cells generate increased heat which needs to be dissipated from the broth.

The heat transfer characteristics of the broth and the vessel (including heat exchanger) impose serious constraints on the reaction scale possible (see Table 1). While the particular heat load and power requirements are specific to the reaction, the scale of reaction generally approaches limitations as ~10 m$^3$ as in the case of E. coli fermentation (Table 1). The amount of heat to be dissipated becomes excessive due to limits on heat transfer coefficients of the broth and vessel. Consequently, the system of vessel and broth will rise in temperature. Unfortunately, biological compounds often have a relatively low upper limit on temperature for which to survive (<45° C. for many). Additionally, power consumption to disperse nutrients and oxygen and coolant requirements to control temperature make the process economically unfeasible (see Table 1).

TABLE 1

Oxygen- and Heat- Transfer Requirements for E. coli: Effects of Scale

| OTR (mmol/L · h) | Volume$^a$ (m$^3$) | Pressure (psig) | Power (hp) | Heat Load (Btu/h) | Coolant$^b$ (° F.) |
|---|---|---|---|---|---|
| 150 | 1 | 15 | 5.0 | 84000 | 40 |
| 200 | 1 | 25 | 4.9 | 107000 | 40 |
| 300 | 1 | 35 | 7.1 | 161000 | 40 |
| 400 | 1 | 35 | 6.9 | 208000 | 40 |
| 150 | 10 | 15 | 50.2 | 884000 | 40 |
| 200 | 10 | 25 | 50.0 | 1078000 | 40 |
| 300 | 10 | 35 | 75.7 | 1621000 | 22 |
| 400 | 10 | 35 | 77.0 | 2096000 | 5 |

$^a$Liquid volume
$^b$Coolant flow is 35 gal/mm for 1-m$^3$ vessel and 100 gal/mm for 10-m$^3$ vessel
$^c$Charles, M. and Wilson, J. Fermentor Design; In: Bioprocess Engineering; Lydersen, B. K., D'Elia, N. A., Nelson, K. L., Ed.; John Wiley & Sons, Inc., New York, 1994.

Aside from reactor scalability, the design of conventional fermentors has other drawbacks. Due to the batch and semi-batch nature of the process, product throughput is low. Also, the complexity and coupled nature of the reaction parameters, as well as the requirement of narrow ranges for these parameters, makes control of the system difficult. Internal to the system, heterogeneity in nutrient and oxygen distribution due to mixing dynamics creates pockets in the broth characterized by insufficient nutrients or oxygen resulting in cell death. Finally, agitation used to produce as homogeneous a solution as possible (typically involving impellar string to simultaneously mix both cells and feeds of oxygen and nutrients) causes high strains which can fracture cell membranes and cause denaturation.

While a wide variety of useful reactors for a variety of chemical and biological reactions, on a variety of size scales exist, a need exists in the art for improved reactors. In particular, there is a current need to significantly improve the design of bioreactors especially as the pharmaceutical and biomedical industries shift increasingly towards bioprocessing.

SUMMARY OF THE INVENTION

The present invention provides systems, methods, and reactors associated with small-scale chemical or biochemical reactions.

In one aspect the invention provides a chemical or biochemical reactor. The reactor includes a reaction unit including a chamber having a volume of less than one milliliter. The chamber includes an inlet connectable to a source of a chemical or biological starting material and an outlet for release of a product of a chemical or biological reaction involving the starting material. A collection chamber is connectable to the outlet of the reaction chamber. The collection chamber has a volume of greater than one liter.

In another aspect the invention involves a chemical or biochemical reactor system. The system includes a mixing chamber including a plurality of inlets connectable to a plurality of sources of chemical or biochemical reagents, and an outlet. A reaction chamber is connectable to and removable from the mixing chamber, and has a volume of less than one milliliter. The reaction chamber includes an inlet connectable to and removable from the outlet of the mixing chamber, and an outlet for release of a product of a chemical or biological reaction involving the starting material.

In another aspect the invention provides methods. One method includes carrying out a chemical or biological reaction in a plurality of reaction chambers operable in parallel, where each reaction chamber has a volume of less than one milliliter. Product of the reaction is discharged from the plurality of reaction chambers simultaneously into a collection chamber having a volume of greater than one liter.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

The present invention provides a chemical or biochemical reactor that can be used for a variety of very small-scale techniques. In one embodiment, a microreactor of the invention comprises a matrix of a few millimeters to a few centimeters in size containing reaction channels with dimensions on the order of hundreds of microns. Reagents of interest are allowed to flow through these microchannels, mixed, and reacted together. The products can be recovered, separated, and treated within the system. While one microreactor may be able only to hold and react a few microliters of the substances of interest, the technology allows for easy scalability and tremendous parallelization. With enhanced oxygen and nutrient distribution, a microreactor of the invention demonstrates increased performance in terms of cell viability. The microreactor geometry resembles closely the natural environment of cells whereby diffusional oxygen and nutrient transfer take place through a high surface area, thin layer interface.

With regard to throughput, an array of many microreactors can be built in parallel to generate capacity on a level exceeding that allowed by current vessels and more uniform in product quality than can be obtained in a batch method. Additionally, an advantage is obtained by maintaining production capacity at the scale of reactions typically performed in the laboratory. In general, the coupled parameters for heat and mass transfer that are determined on the lab-scale for a process do not scale linearly with volume. With conventional reactors, as the magnitude of volume is increased 1,000-1,000,000 times for production, these parameters need to be re-evaluated, often involving a large capital-investment. The use of small production volumes, although scaled in parallel, reduces the cost of current scale-up schemes.

Furthermore, the process can be implemented on a simple platform, such as an etched article for example, a silicon wafer. With the effort of semiconductor manufacturing being towards the reduction in the dimensions of channels, an opportunity to utilize excess capacity within these production facilities (with unused equipment for the larger dimensions) is provided. Mass production of these units can be carried out at very low cost and an array of many reactors, for example thousands of microreactors typically can be built for a price lower than one traditional bioreactor.

Figure 1:
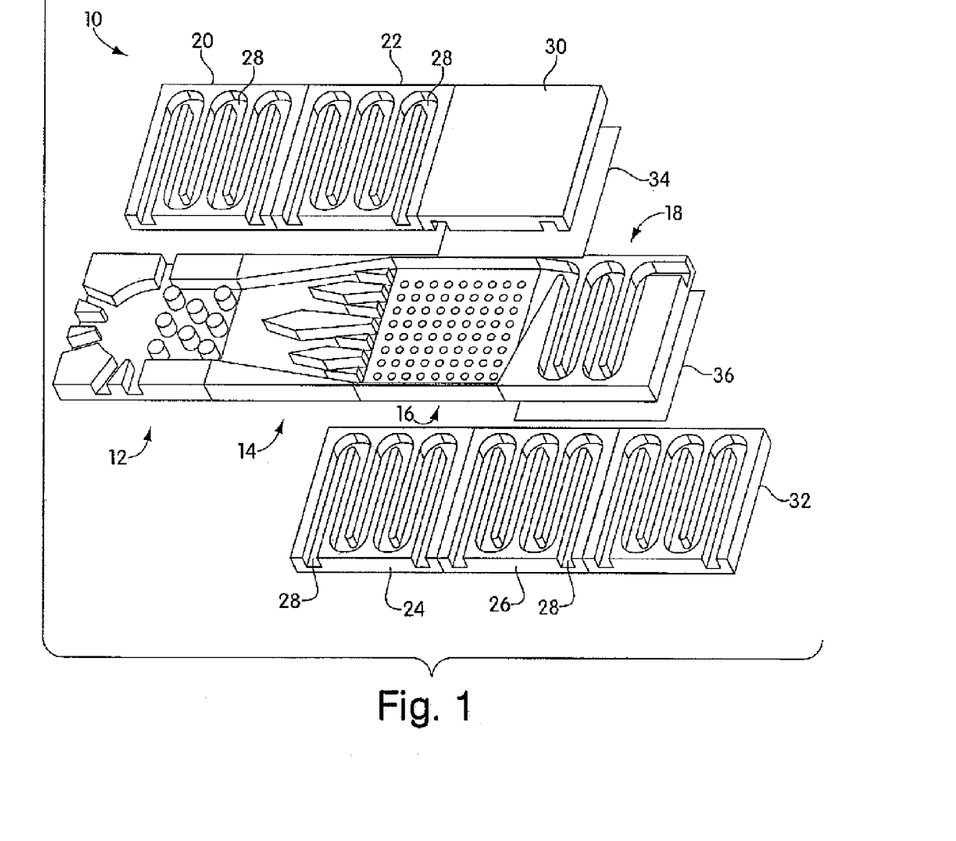
FIG. 1 illustrates a microbioreactor of the invention including mixing, heating/dispersion, reaction, and separation units, in expanded view.

Referring now to FIG. 1, a chemical or biochemical reactor in accordance with one embodiment of the invention is illustrated schematically. The reactor of FIG. 1 is, specifically, a microbioreactor for cell cultivation. It is to be understood that this is shown by way of example only, and the invention is not to be limited to this embodiment. For example, systems of the invention can be adapted for pharmaceutical production, hazardous chemical production, or chemical remediation of warfare reagents, etc.

Microreactor 10 includes four general units. A mixing unit 12, a heating/dispersion unit 14, a reaction unit 16, and a separation unit 18. That is, in the embodiment illustrated, processes of mixing, heating, reaction, purification are implemented in series. Although not shown, pressure, temperature, pH, and oxygen sensors can be included, for example embedded within the network to monitor and provide control for the system. Due to the series format, the opportunity for several reaction units in series for multi-step chemical syntheses, for several levels of increased purification, or for micro-analysis units is provided as well.

Figure 1A:
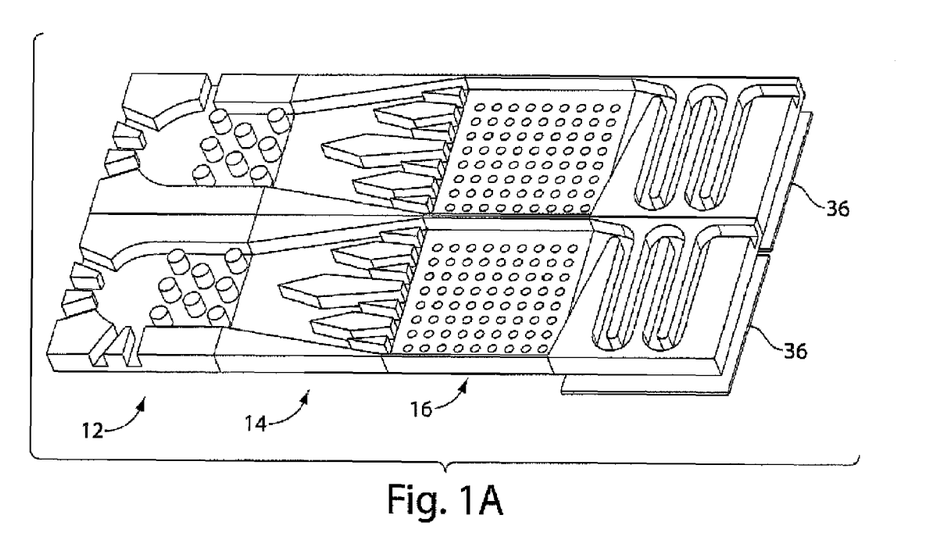
FIG. 1A illustrates a microbioreactor of the invention including various mixing, heating/dispersion, reaction, and separation units, in expanded view.

FIG. 1 shows microreactor 10 in expanded view. As illustrated, each of units 14 and 16 (heating/dispersion and reaction units, respectively) includes at least one adjacent temperature control element 20-26 including a channel 28 through which a temperature-control fluid can be made to flow. As illustrated, temperature control units 20 and 24 are positioned above and below unit 14 and units 22 and 26 are positioned above and below unit 16. Separation unit 18 includes upper and lower extraction solvent fluid units 30 and 32, respectively, separated from unit 18 by membranes 34 and 36, respectively. FIG. 1A shows a similar microreactor having more than one reaction unit (certain elements removed for purposes of clarity).

Figure 2:
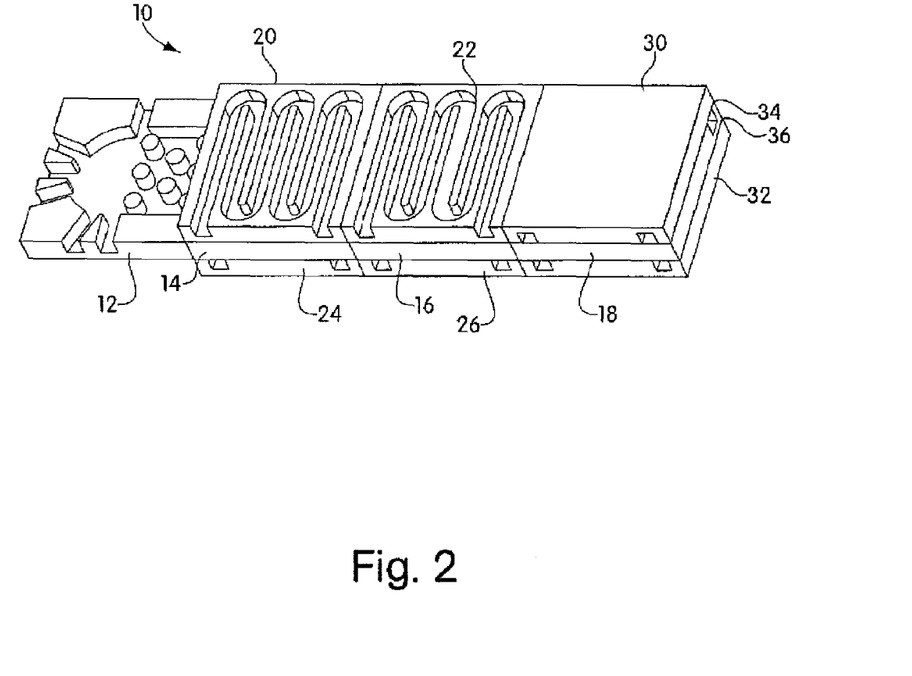
FIG. 2 illustrates the system of FIG. 1 as assembled.

Referring now to FIG. 2, reactor 10 is illustrated as assembled. The individual units of microreactor 10 will now be described in greater detail.

Figure 3:
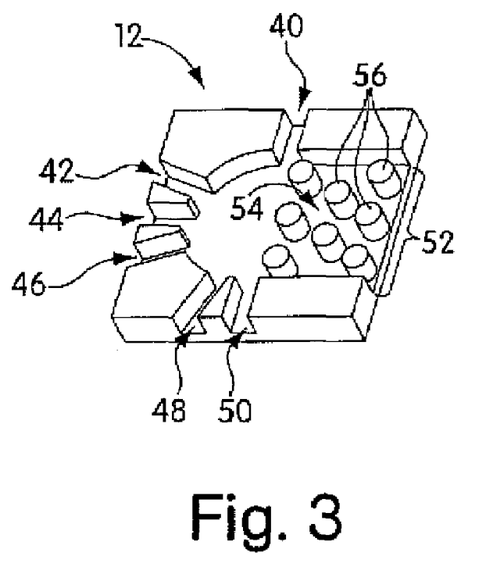
FIG. 3 illustrates the mixing unit of the system of FIG. 1.

Referring now to FIG. 3, mixing unit 12 is illustrated. Mixing unit 12 is designed to provide a homogeneous mixture of starting materials or reactants to be provided to the reaction units, optionally via the heating/dispersion unit. In the specific example of the microbioreactor, mixing unit 12 is designed to provide a homogeneous broth with sufficient nutrients and oxygen, and at the required pH, for cells. Rather than combine the mixing process with simultaneous nourishment of the cells, the process is performed in a preliminary stage and then fed to the reaction stage where cells are immobilized. In this manner, the cells do not experience any shear stress due to mixing and a homogeneous mixture of feed requirements is guaranteed.

As is the case for other components of the reactor, mixing unit 12 can be manufactured using any convenient process. In preferred embodiments the unit is etched into a substrate such as silicon via known processes such as lithography. Other materials from which mixing unit 12, or other components of the systems of the invention can be fabricated, include glass, fused silica, quartz, ceramics, or suitable plastics. Silicon is preferred. The mixing unit includes a plurality of inlets 40-50 which can receive any of a variety of reactants and/or fluid carriers. Although six inlets are illustrated, essentially any number of inlets from one to tens of hundreds of inlets can be provided. Typically, less than ten inlets are needed for a given reaction. Mixing unit 12 includes an outlet 52 and, between the plurality of inlets and the outlet, a mixing chamber 54 constructed and arranged to coalesce a plurality of reactant fluids provided through the inlets. It is a feature of the embodiment illustrated that the mixing chamber is free of active mixing elements. Instead, the mixing chamber is constructed to cause turbulence in the fluids provided through the inlets thereby mixing and delivering a mixture of the fluids through the outlet without active mixing. Specifically, the mixing unit includes a plurality of obstructions 56 in the flow path that causes mixture of fluid flowing through the flow path. These obstructions can be of essentially any geometrical arrangement. As illustrated, they define small pillars about which the fluid must turbulently flow as it passes from the inlets through the mixing chamber toward the outlet. As used herein "active mixing elements" is meant to define mixing elements such as blades, stirrers, or the like which are movable relative to the reaction chamber itself, that is, movable relative to the walls defining the reaction chamber.

The volume of the mixing chamber, that is, the volume of the interior of mixing unit 12 between the inlets and the outlet, can be very small in preferred embodiments. Specifically, the mixing chamber generally has a volume of less than one liter, preferably less than about 100 microliters, and in some embodiments less than about 10 microliters. The chamber can have a volume of less than about five microliters, or even less than about one microliter.

Specifically, in the microbioreactor illustrated, six separate feed streams empty into the mixing chamber under pressure. One feed stream provides gaseous oxygen ($O_2$) as a cell requirement. One stream, respectively, provides carbon dioxide ($CO_2$) and nitrogen ($N_2$) for altering pH. The remaining three channels provide the broth solution including solvent and nutrients. One of these latter streams can also be utilized to provide any additional requirements for the system such as antifoaming agents. Antifoaming agents are sometimes necessary to prevent production of foam and bubbles that can damage cells within the broth. The feed of the various streams into the chamber provides enough turbulence for mixing of the different streams. Flow within microfluidic devices is characterized by a low Reynolds number indicating the formation of lamina. While the turbulence created by the injection streams should provide sufficient mixing before the development of laminar flow, pilon-like obstructions 56 are placed in the flow path of the stream leaving the primary mixing chamber in order to enhance mixing of the lamina. By splitting a main stream into substreams followed by reunification, turbulence is introduced in the flow path, and a mechanism other than simple diffusion is used to facilitate further mixing. The length of this mixing field can be lengthened or shortened depending on the system requirements.

Figure 4:
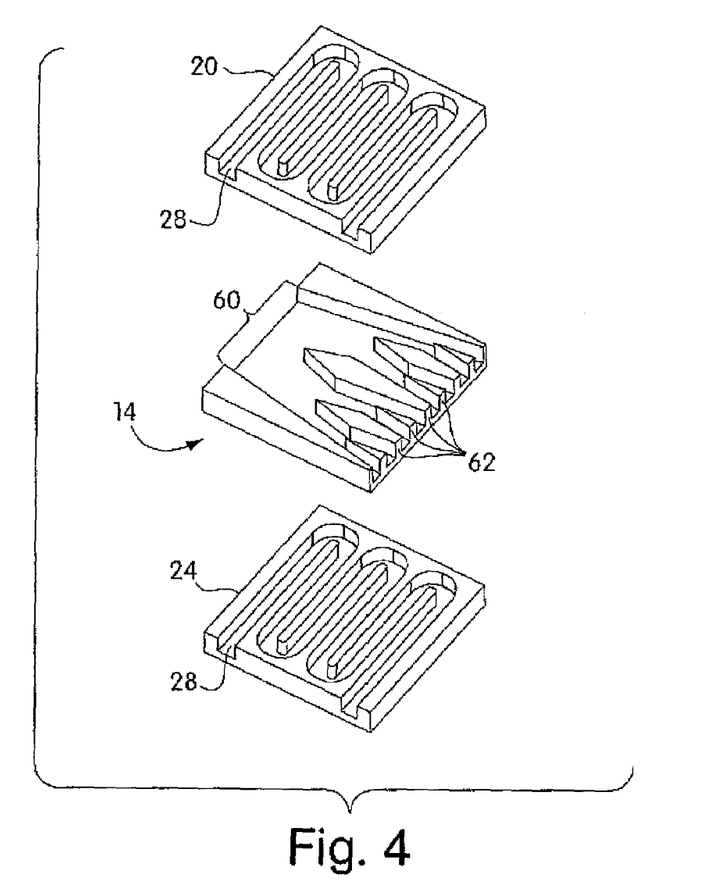
FIG. 4 is an expanded view of the heating/dispersion unit of the system of FIG. 1.

Referring now to FIG. 4, heating/dispersion unit 14 is shown. Unit 14 can be formed as described above with respect to other units of the invention. Unit 14 includes an inlet 60 in fluid communication with a plurality of outlets 62 in embodiments where dispersion as described below is desirable. In operation, a stream of homogeneous fluid exiting the mixing unit (feed broth in the specific microbioreactor embodiment shown) enters a dispersion matrix defined by a plurality of obstruction dividing the stream into separate flow paths directed toward the separate outlets 62. The dispersion matrix is sandwiched between two temperature control elements 20 and 24 which, as illustrated, include fluid flow channels 28 etched in a silicon article. Control unit 24 is positioned underneath unit 14, thus etched channel 28 is sealed by the bottom of unit 14. Control unit 20 is positioned atop unit 14 such that the bottom of unit 20 seals and defines the top of diffusion unit 14. A cover (not shown) can be placed a top unit 20 to seal channel 28.

Rather than for mixing, as in the previous case (FIG. 3), the splitting of the streams is to disperse the medium for its entrance into the reactive chamber in the next unit operation. In traditional reactor systems, fluid flow about a packing material containing catalysts produces the desired reaction. However, if the fluid is not evenly dispersed entering the chamber, the fluid will flow through a low resistance path through the reactor and full, active surface area will not be utilized. Dispersion in this case is to optimize reactor efficiency in the next stage.

With regard to the heating function of this unit, the platform functions as a miniaturized, traditional heat exchanger. Etched silicon platforms both above and below the central platform serve to carry a heated fluid. Cells typically require their environment to have a temperature of ~30° C. The fluids flowing in the etched coils both above and below the broth flow channel heating the broth through the thin silicon layer. The temperature of the fluid in the upper and lower heat exchangers can be modified to ensure proper temperature for the broth. Additionally, the platform can be extended for increased heating loads.

Although a combination heating/dispersion unit is shown, unit 14 can be either a dispersion unit or a heating unit. For example, dispersion can be provided as shown, without any temperature control. Alternatively, no dispersion need be provided (inlet 60 can communicate with a single outlet 62, which can be larger than the outlets as illustrated) and heating units can be provided. Cooling units can be provided as well, where cooling is desired. Units 20 and 24 can carry any temperature-control fluid, whether to heat or cool.

Figure 5:
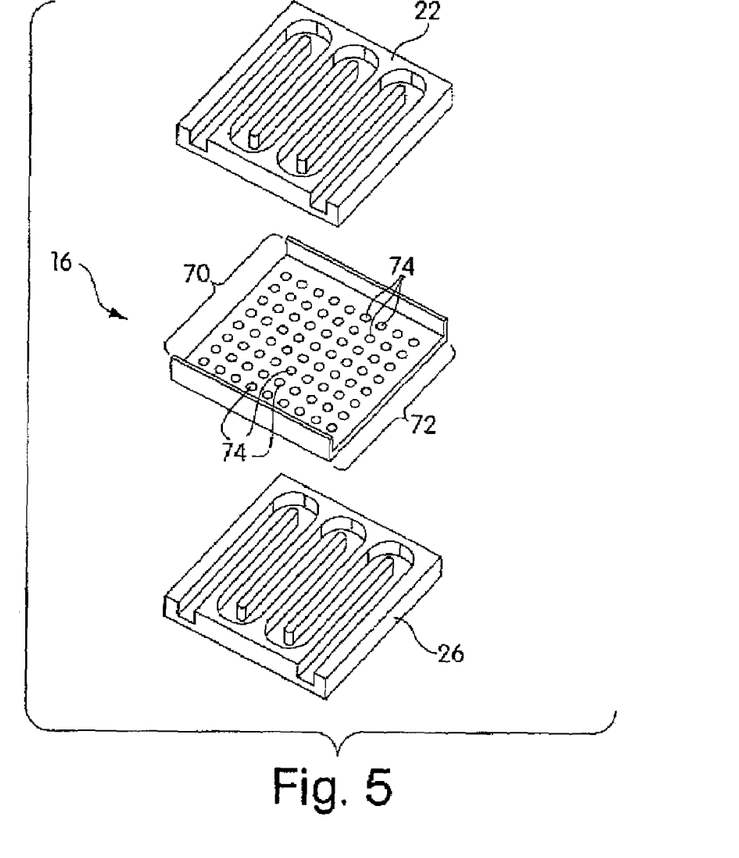
FIG. 5 is an expanded view of the reaction chamber of the system of FIG. 1.

Referring now to FIG. 5, reaction chamber 16 is shown, including temperature control units 22 and 26, in expanded form. Units 22 and 26 can be the same as units 20 and 24 as shown in FIG. 4, with unit 22 defining the top of reaction chamber 16. Reaction unit 16 includes an inlet 70 fluidly communicating with an outlet 72 and a reaction chamber defined therebetween. The reaction chamber, in microreactor embodiments of the invention, has a volume of less than one milliliter, or other lower volumes as described above in connection with mixing unit 12. Inlet 70 is connectable to a source of a chemical or biological starting material, optionally supplied by mixing unit 12 and heating/dispersion unit 14, and outlet 70 is designed to release the product of a chemical or biological reaction occurring within the chamber involving the starting material. Unit 16 can be formed from materials as described above.

The reactor unit is the core of the process. While the unit is designed to be interchangeable for biological or pharmaceutical reactions, the specific application as shown is for cell cultivation. As in the case of the previous unit, temperature control units such as heat exchanger platforms will sandwich the central reaction chamber. The heat exchangers will maintain the temperature of the reaction unit as the same temperature as discussed for the cell broth.

A feature of the unit is heterogeneous reaction on a supported matrix. Cell feed enters the reaction chamber under the proper pH, $O_2$ concentration, and temperature for cell cultivation. Cells, immobilized onto the silicon framework at locations 74 either by surface functionalization and subsequent reaction or entrapment within a host membrane, metabolize the nutrients provided by the feed stream and produce a product protein. The initial reaction platform can be a two-dimensional array of cells both on the top and bottom of the reaction chamber. This arrangement is to prevent a large pressure drop across the unit which would be detrimental to flow.

In this unit, oxygen and nutrients are diffused from the flowing stream to the immobilized cells. The cells, in turn metabolize the feed, and produce proteins which are swept away in the flowing stream. The flowing stream then enters the fourth chamber which removes the protein product from the solution.

Referring again to FIG. 1, it can be seen how dispersion unit 14 creates an evenly-divided flow of fluid (reactant fluid such as oxygen and nutrients in the case of cell cultivation) across each of locations 74 in reaction to chamber 16.

Figure 6:
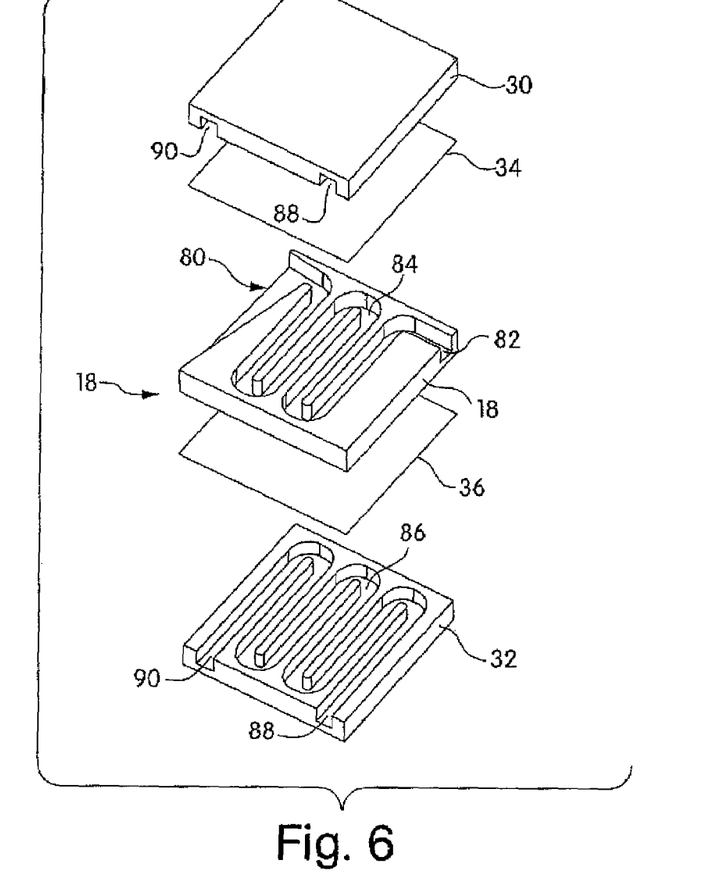
FIG. 6 is an expanded view of the separation unit of the system of FIG. 1.

Referring now to FIG. 6, separation unit 18 is shown in greater detail, in expanded view. Separation unit 18 defines a central unit including an inlet 80 communicating with an outlet 82, and a fluid pathway 84 connecting the inlet with the outlet. Unit 18 can be fabricated as described above with respect to other components of the invention, and preferably is etched silicon. It may be desirable for fluid path 84 to completely span the thickness of unit 18 such that the pathway is exposed both above and below the unit. To maintain structural integrity, pathway 84 can be etched to some extent but not completely through unit 18 as illustrated, and a plurality of holes or channels can be formed through the bottom of the pathway exposing the bottom of the pathway to areas below the unit. Inlet 80 can be connectable to the outlet of reaction chamber 16, and outlet 82 to a container for recovery of carrier fluid.

In the embodiment illustrated, membranes 34 and 36 cover exposed portions of fluid pathway 84 facing upward or downward as illustrated. Membranes 34 and/or 36 can be any membranes suitable for separation, i.e. extraction of product through the membrane with passage of effluent, or carrier fluid, through outlet 82. Those of ordinary skill in the art will recognize a wide variety of suitable membranes including size-selective membranes, ionic membranes, and the like. Upper and lower extraction solvent fluid units 30 and 32, which can comprise materials as described above including etched silicon, each include a fluid pathway 86 connecting an inlet 88 with an outlet 90. Fluid pathway 86 preferably is positioned in register with fluid pathway 84 of unit 18 when the separation unit is assembled. In this way, two flowing streams of solvent through channels 86 of units 30 and 32 flow counter to the direction of flow of fluid in channel 84 of unit 18, the fluids separated only by membranes 34 and 36. This establishes a counter-current tangential flow filtration membrane system. By concentration gradients, products are selectively extracted from channel 84 into solvent streams flowing within channels 86 and unit 30 or 32. Product is recovered through the outlet 90 of units 30 or 32 and recovered in a container (not shown) having a volume that can be greater than 1 liter. Outlets 90 thereby define carrier fluid outlets, and a fluid pathway connects inlet 80 of unit 18 with the carrier fluid outlets 90 of units 30 and 32, breached only by membranes 34 and 36. Carrier fluid outlet 82 can be made connectable to a recovery container for recycling of reaction carrier fluids. In the example of a microbioreactor, residual oxygen and nutrients are recovered from outlet 82 and recycled back into the feed for the process.

The flowing streams of extraction solvent in channels 86 can be set at any desired temperature using temperature control units (not illustrated). In the case of a microbioreactor, these fluids can be set at approximately 4° C. The low temperature is needed to maintain the efficacy of the protein products and prevent denaturation. Additionally, several purification and clarification steps are often performed in industrial application. The necessity of further purification is remedied by the use of additional units in series.

Embedded within the production process can be control systems and detectors for the manipulation of temperature, pH, nutrients, and oxygen concentration. Where a microbiorector is used, the viability of cells is dependent upon strict limits for the parameters mentioned above. Narrow set-point ranges, dependent on the cell system selected, can be maintained using thermocouples, pH detectors, $O_2$ solubility detectors, and glucose detectors between each unit. These measurements will determine the heat exchanger requirements, $O_2$, $CO_2$, $N_2$, and nutrient inputs.

Diaphragm and peristaltic pumps can be used to provide the necessary driving force for fluid flow in the units. Such pumps are also used to maintain flow in the heat exchanger units.

It is a feature of the invention that many of the microreactors as illustrated can be arranged in parallel. Specifically, at least ten reactors can be constructed to operate in parallel, or in other cases at least about 100, 500, 1,000, or even 10,000 reactors can be constructed to operate in parallel. These reactors can be assembled and disassembled as desired.

It is another feature of the invention that individual units 12, 14, 16, and 18 can be constructed and arranged to be connectable to and separable from each other. That is, any arrangement of individual components can be created for a desired reaction. For example, with reference to FIG. 1, heating/dispersion unit 14 may not be necessary. That is, outlet 52 of mixing unit 12 can be connectable to either inlet 60 of heating/dispersion unit 14, or inlet 70 of reaction unit 16 where a heating/dispersion unit is not used. Moreover, assembly and disassembly of reactors to create a system including many, many reactors operating in parallel, as described above, or in series is possible because of the connectability and separability of the components from each other to form systems containing specific desired components, and any number of those or other systems operating together. Equipment for connection and separation of individual components of a reactor can be selected among those known in the art, as can systems for connection of a variety of reactors in parallel or in series. Systems should be selected such that the individual components can be connectable to and separable from each other readily by laboratory or production-facility technicians without irreversible destruction of components such as welding, sawing, or the like. Examples of known systems for making readily reversible connections between components of reactors or between reactors to form parallel reactors or series reactors include male/female interconnections, clips, cartridge housings where components comprise inserts within the housings, screws, or the like.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described. In the claims the words "including", "carrying", "having", and the like mean, as "comprising", including but not limited to.

What is claimed is:

1. A system for maintaining and cultivating cells in culture and obtaining a protein resulting from interaction of the cells with oxygen and/or nutrients and/or other components, comprising:
    a small-scale chemical or biochemical reactor comprising a plastic substrate comprising at least one reaction unit, the reactor comprising an inlet, an outlet, and a fluid pathway connecting the inlet and the outlet, the fluid pathway comprising a chamber having a surface suitable for cell growth and a volume of less than about 1 ml, the chamber being constructed and arranged to maintain and cultivate cells in culture, the chamber further comprising an inlet fluidly connectable to a source of nutrients for the cells having a controlled pH, and an outlet for release of the protein resulting from the interaction involving the cells in the chamber;
    a membrane defining at least one wall of the fluid pathway;
    an enclosure positioned proximate the membrane, wherein at least one product of the interaction involving cells in the chamber passes across the membrane into the enclosure;
    the reactor further comprising a pH sensor.

2. A system for maintaining and cultivating cells in culture and obtaining a protein resulting from interaction of the cells with oxygen and/or nutrients and/or other components, comprising:
    a small-scale chemical or biochemical reactor comprising a plastic substrate comprising at least one reaction unit, the reactor comprising an inlet, an outlet, and a fluid pathway connecting the inlet and the outlet, the fluid pathway comprising a chamber having a surface suitable for cell growth and a volume of less than about 1 ml, the chamber being constructed and arranged to maintain and cultivate cells in culture, the chamber further comprising an inlet fluidly connectable to a source of nutrients for the cells having a controlled pH, and an outlet for release of the protein resulting from the interaction involving the cells in the chamber;
    a membrane defining at least one wall of the fluid pathway;
    an enclosure positioned proximate the membrane, wherein at least one product of the interaction involving cells in the chamber passes across the membrane into the enclosure;
    the reactor further comprising an oxygen sensor.

3. A system as in claim 1, further comprising means for controlling the temperature of the chamber to maintain a temperature suitable for cultivating cells to generate the protein resulting from interaction of the cells with oxygen and/or nutrients and/or other components.

4. A system as in claim 1, further comprising a mixing unit fluidly connectable to the inlet of the chamber, the mixing unit including an outlet connectable to the inlet of the chamber, a plurality of inlets each in fluid communication with the outlet and a mixing chamber between plurality of inlets and of the outlet.

5. A system as in claim 4, wherein the mixing chamber is free of active mixing elements.

6. A system as in claim 2, wherein the system comprises a plurality of reaction units attachable to and separable from each other, the plurality of reaction units being constructed and arranged to operate in parallel.

* * * * *